United States Patent [19]

Avrameas et al.

[11] Patent Number: 4,729,961
[45] Date of Patent: * Mar. 8, 1988

[54] PROCESS FOR THE DETECTION AND ASSAY BY ERYTHROADSORPTION

[75] Inventors: Stratis Avrameas, La Celle Saint Cloud; Jean-Luc Guesdon, Paris, both of France

[73] Assignee: Institut Pasteur, Paris, France

[*] Notice: The portion of the term of this patent subsequent to Jul. 2, 2002 has been disclaimed.

[21] Appl. No.: 807,773

[22] Filed: Dec. 11, 1985

Related U.S. Application Data

[63] Continuation of Ser. No. 355,744, Feb. 1, 1982, abandoned.

[30] Foreign Application Priority Data

Jul. 9, 1980 [FR] France .................. 80 15293

[51] Int. Cl.$^4$ .................. G01N 33/566; G01N 33/555
[52] U.S. Cl. .................. 436/501; 436/520; 436/521; 436/522; 436/531; 436/809; 436/819; 436/825; 436/827; 435/7; 435/188; 435/6
[58] Field of Search .................. 436/501, 503, 506, 507, 436/508, 518, 519–522, 528–535, 805, 819, 821, 822, 823, 809, 825, 827; 435/2, 4, 6, 7, 28, 29, 174, 181, 188, 177

[56] References Cited

U.S. PATENT DOCUMENTS

| | | | |
|---|---|---|---|
| 3,385,757 | 11/1963 | Finter | 436/522 |
| 3,553,310 | 1/1971 | Csizmas et al. | 436/521 |
| 3,565,987 | 2/1971 | Schuurs | 436/520 |
| 3,852,157 | 12/1974 | Rubenstein et al. | 435/188 |
| 4,130,634 | 12/1978 | Molinaro et al. | 436/522 |
| 4,134,792 | 1/1979 | Boguslaski et al. | 435/7 |
| 4,152,411 | 5/1979 | Schall, Jr. | 436/500 |
| 4,193,982 | 3/1980 | Avrameas et al. | 436/520 |
| 4,228,237 | 10/1980 | Hevey et al. | 435/7 |
| 4,241,176 | 12/1980 | Avrameas et al. | 435/181 |
| 4,298,685 | 11/1981 | Parikh et al. | 435/810 |
| 4,320,111 | 3/1982 | Hirsch et al. | 435/4 |
| 4,342,826 | 8/1982 | Cole | 435/810 |
| 4,399,217 | 8/1983 | Holmquist et al. | 435/7 |
| 4,403,037 | 9/1983 | Coates | 436/521 |
| 4,526,871 | 7/1985 | Avrameas et al. | 435/7 |

FOREIGN PATENT DOCUMENTS

1210819 11/1970 United Kingdom .................. 436/520

OTHER PUBLICATIONS

*Basic and Clinical Immunology*, 4th Edition, Stites, D. P. et al. editors, Lange Medical Publications, Los Altos, pp. 356–358 (1982).
Gvesdon et al., "The Use of Ardin–Biotin . . . ", published in the Journal of Histochem. and Cytochem., vol. 27, #8, pp. 1131–1139, 1979.
Chem. Abstr., vol. 81, cite 61897(s), p. 335, 1974.
Chem. Abstr., vol. 91, cite 209046(t), p. 491, 1979.

*Primary Examiner*—Margaret Moskowitz
*Attorney, Agent, or Firm*—Frost & Jacobs

[57] ABSTRACT

A process for the detection and assay of a biological substance by erythroadsorption by immobilizing a substance having a binding affinity for the biological substance to be assayed; incubating the immobilized substance with a liquid medium containing the biological substance to be assayed, forming a fixed substance; incubating the fixed substance with a coupling product comprising a specific ligand and a second ligand which binds with erythrocytes; adding erythrocytes; and determining the amount of erythrocytes bound to the coupling product. The determination of the amount of bound erythrocytes can be made visually with the naked eye or determined by lysis of the erythrocytes bound to the coupling product and quantitatively measuring the released hemoglobin. The specific ligand can be an antibody or an antigen and the second ligand capable of coupling erythrocytes can, for example, be red blood cell antibodies.

12 Claims, 1 Drawing Figure

PROCESS FOR THE DETECTION AND ASSAY BY ERYTHROADSORPTION

This is a continuation of application Ser. No. 355,744, filed Feb. 1, 1982, now abandoned.

BACKGROUND OF THE INVENTION

The present invention relates to a process for detecting and assaying a biological substance by erythroadsorption.

Many biological techniques exist for the localization, detection and assay of biological substances. Mention may be made, for example, of immunoenzymatic techniques (immunoenzymatic assays or histochemical detection), immunofluorescence (immunofluormetrical assay or histochemical detection), the radioimmunologic process, the hemagglutination technique and the like.

As reagents, these techniques make use of substances labelled with an enzyme, a fluorochrome or a radioisotope or sensitized red blood cells.

The hemagglutination technique for antibody determination consists in mixing erythrocytes (red blood cells) sensitized by an antigen with a solution containing the antibody to be determined or assayed. This technique is effected in liquid phase. For fuller details about the technique of hemagglutination, reference may be made to the following work, cited as a reference: "Handbook of experimental immunology", 3 vol., Ed. D. M. WEIR, (1978) Blackwell Scientific.

As references illustrating the use of sensitized erythrocytes in processes for the detection or the assay of antigens or antibodies the following references may be mentioned.

German patent application No. 2,732,554 relates to an indicator system for antibody-antigen reactions presented in the form of a gel matrix. This system consists of erythrocytes to which are coupled antibodies or antigens in the presence of a specific buffer and a complement. This system therefore involves erythrocytes sensitized with an antibody or an antigen.

U.S. Pat. No. 4,130,634 relates to a process for detecting the presence of a particular antigen in a composition. This process consists in contacting compositions with erythrocytes to which are coupled specific antibodies of said antigen, in adding a development agent comprising an antibody reacting with said antigen, in adding the complement and in noting the lysis of said erythrocytes as a positive indication of the presence of said antigen.

The the summary of Chemical Abstracts vol. 81, No. 11 of the Sept. 16, 1974, relates to an assay on plates by local hemolysis with sheep erythrocytes sensitized by antigens.

It will be also noted that it was suggested to submit the erythrocytes to a preliminary treatment with one or more tanning agents prior to sensitization. In this connection, reference may be made to French Pat. No. 1,516,640.

SUMMARY OF THE INVENTION

A new process for the assay of biological substances has now been found which, as an assay reagent, uses the coupling product of a specific ligand and of a ligand capable of reacting with erythrocytes, and erythrocytes as a detector. The process of the invention makes it possible to avoid the use of erythrocytes sensitized with antibodies or antigens.

The process of the invention is a process for the detection and the assay of a biological substance by erythroadsorption which consists:

(1) in immobilizing a substance having a binding affinity for the biological substance to be assayed;

(2) in incubating this substance with the liquid medium containing the biological substance to be assayed;

(3) in incubating, after washing, the resulting reaction medium with the coupling product of a specific ligand and of a ligand capable of reacting with erythrocytes;

(4) in adding erythrocytes; and (5) in determining erythroadsorption.

The process of the invention is suited to assay, various biological substances such as, antigens, antibodies, haptens, hormones, immunoglobulines and other substances of biological interest.

The substance having a binding affinity with respect to the biological substance to be assayed can be any substance capable of being bound in a specific manner to said biological substance. For example, if the biological substance to be assayed is an antibody, the substance having a coupling affinity will then be an antigen, and vice versa.

The substance having a binding affinity for the biological substance to be assayed is immobilized on any substrate by conventional techniques.

As a substrate, any insoluble substrate can be used which is possible to form into a receptacle. As a substance constituting such substrates, use may be made of cellulose and derivatives thereof, polyacrylamide, alkyl polymethacrylates and other polymers of natural or synthetic origin as well as glass.

It is advantageous to use microplates to immobilize the substance having an affinity for the biological substance to be assayed, for example, polystyrene microplates. It has been observed that microplates having U or V shaped cross sectional cavities were the most suitable.

The coupling product used as an assay reagent according to the invention is the coupling product of a specific ligand and a ligand capable of reacting with erythrocytes. It also constitutes an object of the invention.

In the present specification, "specific ligand" means any soluble substance that can react in a specific manner with the substance having an affinity for the biological substance to be assayed, or with the biological substance itself.

In the present specification, "soluble substance" designates any substance soluble in the media currently used for biological reactions. They may be aqueous media such as physiological media, or mixtures of aqueous and organic media.

Furthermore, the specific ligand used must be such that the coupling product specific ligand-ligand capable of reacting with erythrocytes is soluble in an aqueous medium.

According to the invention, "aqueous media" designates aqueous media, whether buffered or not, currently used in the biological field, such as phosphate buffer solutions, buffer solutions containing a detergent such as "Tween" or gelatine, bovine serum albumine, bovine lactalbumin and other substances usually used in such fields.

The specific ligands which comply with such a definition are notably, antibodies, macromolecular antigens, haptenes, hormones and their receptors, and similar substances. Among the specific ligands mentioned above, antibodies and antigens are most commonly used.

The ligand capable of reacting with erythrocytes is a substance possessing recognition sites of specific determinants of erythrocytes or of substances coupled to erythrocytes. In French patent application No. 80,11,470 there is described a coupling product of a lectin and a specific ligand and its applications in the biological field, notably for the assay of biological substances wherein the labelling agent can be red blood cells.

According to the invention, a substance other than a lectin, complying with the definition given hereinabove, will be used as a ligand capable of reacting with normal or modified erythrocytes. As examples of such ligands there may be mentioned anti-red blood cell-antibodies, avidin, biotin and similar products.

It must be pointed out that avidin and biotin are two substances which strongly interact by the noncovalent way. This strong intersection has also been used in immunoenzymatic techniques, such as the so-called avidin-biotin bridge technique, or the technique using an avidin-labelled enzyme. In this connection, reference may be made to the article by GUESDON et al. (The Journal of Histochemistry and Cytochemistry, vol. 27, No. 8, p. 1131-1139, 1979).

When avidin is used as the ligand capable of reacting with erythrocytes in the process of the invention, modified erythrocytes will be used, that is to say, erythrocytes bearing biotin and vice-versa.

Similarly, it would be possible to use as the ligand capable of reacting with erythrocytes any substance which could interact with a substance bound to erythrocytes. Thus, for the purpose of the invention the term "erythrocytes" designates both normal erythrocytes and modified erythrocytes, i.e., bearing a specific substance of the used ligand and which is defined in a general manner as a ligand capable to reacting with erythrocytes.

The modification of erythrocytes is effected by conventional means within the scope of the one skilled in the art, i.e., by the binding techniques currently used in the biological field (see GUESDON et al article previously mentioned).

It must be pointed out that biotin can be bound to erythrocytes by the use of biotinyl-N-hydroxy succinimide according to the procedure described in the article by JASIEWICZ et al. (Exp. Cell, Res. 1976, 100, 213-217).

The coupling of a specific ligand to a ligand capable of reacting with erythrocytes is effected by a suitable coupling agent, such as, for example, glutaraldehyde and benzoquinone. Coupling is advantageously realized by covalent bonds. It is effected according to a process similar to those used for coupling proteins.

For example, coupling can be effected by a process similar to that described for obtaining antibody-enzyme conjugates in Scand. J. Immunol., vol. 8, supp 7 p. 7-23, 1978. Such a coupling process consists in contacting, in one or more steps, a coupling agent with the substances to be coupled.

Benzoquinone can also be used as coupling agent. As a document illustrating the technique of benzoquinone coupling reference may be made to French Pat. No. 75,37,392 (published as No. 2,337,107).

Determination of erythroadsorption may be effected in several ways. For example, it is possible to visually observe that the red blood cells are adsorbed on the surface of the substrate on which has been immobilized the substance having a binding affinity for the biological substance to be assayed. In this case, the process of the invention makes it possible to identify a particular biological substance in a given biological liquid. If, on the other hand, the biological liquid does not contain the particular biological substance, the erythrocytes are not adsorbed and form a residue in the bottom of the receptacle, for example, the wells of microplates. The process of the invention also makes it possible to quantitatively determine a given biological substance. For this purpose, the red blood cells that have not reacted are removed, by aspiration with a pipette, for example. The adsorbed erythrocytes are then lysed, with distilled water for example, and the substances released by the red blood cells, such as hemoglobuline, or the substance artificially introduced by the experimenter, are determined by spectrophotometry at 403 nm which enables this determination process to be completely automatized.

The hemoglobin may also be assayed by an enzymatic reaction. For example, it is possible to use one of the substrates of peroxidase, such as ortho-dianisidine or ortho-phenylene-diamine. Readings can also be made by spectrophotometry at 400 nm for orthodianisidine and at 492 nm for ortho-phenylene-diamine.

The amount of substances released by the red blood cells, for example, the amount of released hemoglobine is proportional to the amount of the substance to be assayed which makes it possible, for example, to assay an antigen or an antibody present in the sample by reference to a standard scale of hemolysis of red blood cells established under the same conditions.

The process of the invention is particularly well suited for the assay of antibodies and antigens and will be described in greater detail hereinafter, while in no way limiting its scope, referring to the single appended figure, on which is shown the reaction diagram of the process of the invention.

BRIEF DESCRIPTION OF THE DRAWING

In the single FIGURE, (1) shows the first step of the process of the invention during which antigens (Ag) are immobilized on the substrate (10). In the particular case of the FIGURE, the substrate (10) represents a V-shaped well of a microplate. Immobilization of antigens, which in this particular case constitute the substance having an affinity for the biological substance to be assayed, namely, antibodies, is effected, for example, by passive adsorption or, if necessary, by covalent bonding according to the nature of the substrate.

Step (2) consists of an incubation of the immobilized antigen with the biological liquid containing the antibody (Ac) to be assayed, for example, the serum to be titrated. After this incubation step, during which the antigen (Ag) interacts with the corresponding antibody (Ac), (if it is present in the serum to be tested) the substrate is washed with a buffer solution, for example, a phosphate buffer solution optionally containing a detergent such as Tween, referred to hereinafter as PBS or PBS-Tween.

Figure 1:
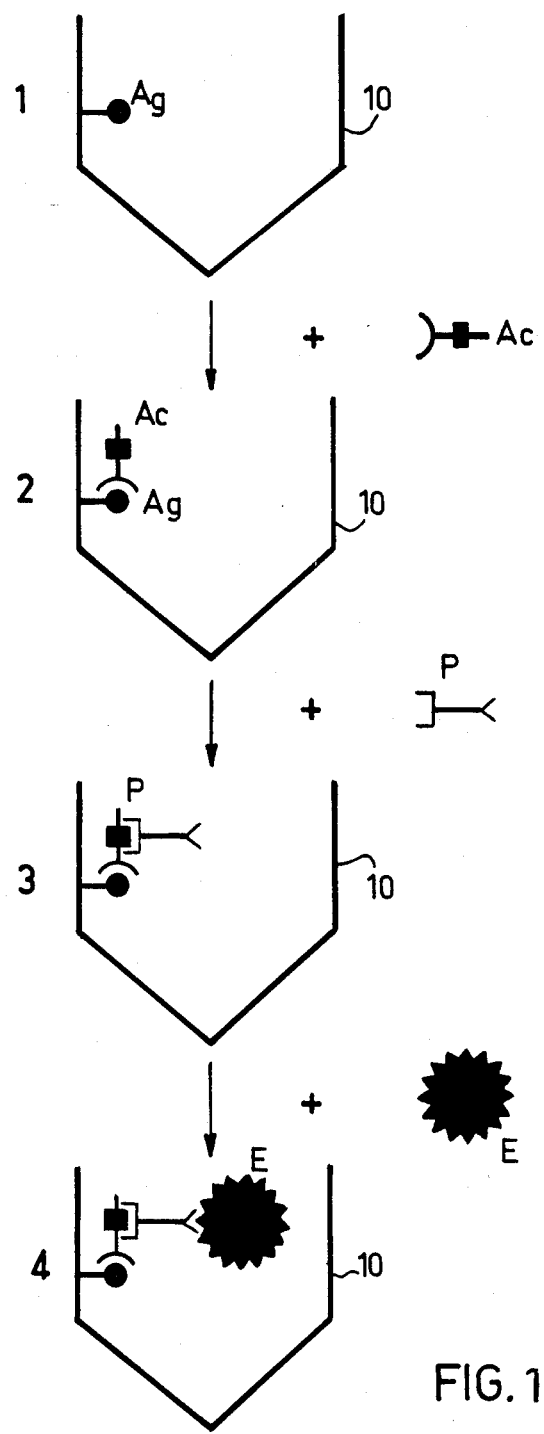

Step (3) of the process of the invention consists in incubating the substrate obtained in step (2) with a coupling product specific ligand-ligand capable of reacting with erythrocytes (P). In this particular case, the specific ligand is an antibody directed against the immunoglobulines of the human or animal species of the serum to be tritated. After this incubation, the resulting system is washed as described hereinabove for removing the coupling product that has not reacted. In step (4), erythrocytes (E) are added and are adsorbed by the coupling product only if the serum to be titrated contains the antibody corresponding to the immobilized antigen, otherwise the erythrocytes are not fixed and fall to the bottom of the receptacle.

In its application in human clinical procedures, the process of the invention makes it possible to rapidly detect the presence of a given antibody in a patient's serum.

The quantitative assay, i.e., the determination of the amount of antibody in the serum, will easily be effected as described hereinabove, that is to say, by lysis of the erythrocytes and determination of the amount of substances released by these erythrocytes, for example, the amount of hemoglobulin.

DESCRIPTION OF THE PREFERRED EMBODIMENT

According to the invention, it is advantageous to use sheep red blood cells for erythroadsorption. As the sera have cross reactions between one species and another, and they often contain anti red blood cell antibodies, such as sheep anti red blood cell antibodies care must be taken to absorb the serum to be tested with red blood cells to avoid false positive reactions. Although such a technique makes use of means known to a man skilled in the art, some of these embodiments for putting it into effect will be given hereinafter.

In the case wherein the antibody or the antigen to be assayed is not thermolabile, this absorption may be effected by subjecting the serum to the following steps which consist:

(a) in decomplementing the serum, i.e., heating it to about 56° C. for about 30 minutes;

(b) in adding an excess of sheep red blood cells to said serum, for example, to obtain a concentration of 10% red blood cells;

(c) in leaving the serum at ambient temperature for about 1 hour under gentle stirring;

(d) in centrifuging to recover the serum absorbed and remove the residue of red blood cells.

In the case wherein the antigen or the antibody to be determined is thermolabile, the serum will not be heated but it will be absorbed by the red blood cells of sheep, for example, and treated with a tanning agent, preferably glutaraldehyde.

The process of the invention is a simple and sensitive process, particularly suited for the detection or the assay of antibodies and of antigens. Its sensitivity is such that it makes it possible to detect an antigen present at a concentration in the order of a nanogramme per milliliter.

It is effected entirely in the solid phase; it requies no separation, centrifugation or filtration steps to put it into effect, apart from that necessitated by the immobilization substrate of one of the reagents (by washing the substrate).

The process of the invention will now be illustrated by the following non-limiting examples:

The source of the products used in the examples is given below.

Specific antibodies isolated by passing entire sera over corresponding immunoadsorbants is prepared by the immobilization of a specific antigen on polyacrylamide agarose beads activated with glutaraldehyde according to the technique described in J. Immunol. Meth., 1876, 11 129–133. Anti human IgE sheep immunsera and anti IgG rabbit immunsera or sheep antierythrocytes were obtained by the hyperimmunization of animals with the corresponding antigen in complete freund's adjuvant (Difco Laboratories Detroit USA) using the technique described in Immunochemistry 1969, 6, 43–53.

Sheep anti red blood cell antibodies were isolated from rabbit immunsera with a glutaraldehyde copolymer of bovine serum albumin and cells stromas according to the process described in Immunochemistry, 1969, 6, 53–66. The enzyme-labelled antibodies used in the comparative example were prepared according to the technique used in Immunochemistry 1969, 6, 43–53.

Bovine serum albumin was sold by POVITE (Amsterdam, Holland).

An aqueous 25% glutaraldehyde solution was supplied by Taad Laboratories (Reading; UK).

"Tween" and biotin were supplied by Merck-Schuchardt (Darmstadt Federal Germany).

Avidin was prepared from egg white and by ion-exchange chromatography on a DEAE cellulose column.

Calf thymus DNA was supplied by Sigma Chemical Co. (St-Louis USA).

Concanavalin A and methyl-alpha-D-mannoside were supplied by Industrie Biologique Francaise (Pharmindustrie).

EXAMPLE 1

Assay of anti-DNA antibodies

In this example, as a coupling produce specific ligand-ligand capable of reacting with erythrocytes, there was used the coupling product of human anti-immunoglobuline antibodies and sheep anti-red blood cell antibodies obtained by the one-step glutaraldehyde coupling procedure described in Immunochemistry, 1969, 6, 43–53.

Prior to the coupling step, the antibodies were dialyzed for one night at 4° C. against a 0.1N phosphate buffer pH 6.8 30 μl of a 1% glutaraldehyde solution was added under gentle stirring to 1 ml of an 0.1M phosphate buffer pH 6.8 containing 2 mg of sheep anti-red blood cell antibodies and 2 mg of human anti-immunoglobulin antibodies. After 3 hours incubation at ambient temperature, 50 μl of a 2M glycine solution was added and, two hours later, the mixture was dialyzed for one night at 4° C. against a buffered saline solution (phosphate buffer). After centrifugation (3000 g, 30 minutes) and the addition of an equal volume of glycerol, the preparation obtained was stored at −20° C. until use.

Polystyrene plates having U or V shaped wells were coated with calf thymus DNA by incubation of 0.2 ml DNA solution (0.5 mg/ml) per well for 2 hours at 37° C. and for 16 hours at 4° C. The DNA was in solution in a 0.1M citrate buffer pH 6.0 containing 0.1M NaCl. 0.2 ml of the serum solution to be tested (containing anti DNA antibodies) in PBS-TWEEN containing 1% bovine serum albumin was added to each well containing DNA and was left to incubate for 16 hours at 4° C. The plates were washed three times with PBS-TWEEN, and 0.2 ml of the coupling product prepared as hereinabove was added in the well. After two hours incubation at 37°

C. the plates were washed three times with PBS-TWEEN and 0.2 ml of a 0.1% sheep red blood cell solution was then added and erythroadsorption was determined. Prior to use, the red blood cells conserved in sterile Elsever medium were washed 10 times by centrifugation with PBS.

This trial was effected with various dilutions of the serum to be tested and the last dilution giving erythroadsorption which was still visible was noted. The results obtained are given in table I below.

The same determination was effected by using as coupling product human anti-immunoglobuline antibodies and avidin obtained by the procedure described hereinabove by using 30 μl of a 1% glutaraldehyde solution and 1 ml of a 0.1M phosphate buffer solution pH 6.8 containing 8 mg avidin and 2 mg human anti-Ig antibodies.

In this trial, the erythrocytes were modified with biotin in accordance with the operating procedure described hereinafter, similar to that described by JA-SIEWICZ et al in Exp. Cell. Res. 1976, 100, 213–217 using biotinyl-N-hydroxysuccinimide. Erythrocytes washed with PBS (10 times) were washed a further 3 times with a 0.10M NaCl solution containing 0.05M NaHCO$_3$. The erythrocytes were combined with biotin by the addition of 7 mg biotinyl-N-hydroxysuccinimide dissolved in 80 μl of dimethylformamide distilled in 2 ml of a 2.5% suspension of erythrocytes. This mixture was incubated for one hour at ambient temperature and washed three times with PBS. Finally, the suspension was adjusted to 0.1% for use in the process of the invention. The results obtained are given in table I below.

By way of comparison, the same determination was effected using as coupling product concanavalin A/anti-human Ig antibodies obtained according to the procedure described in French patent application No. 80 11 470. In this particular case, the human anti Ig antibody coupling product solution used in step 3 of the process contained methyl-alpha-D-mannoside to avoid the concanavalin reacting with the glycosidic fractions present in the serum to be tested and which would falsify erythroadsorption. The results obtained according to this procedure are also given in table I.

Using a procedure similar to the one described hereinabove it was also possible to determine human IgE with a very high degree of sensitivity.

EXAMPLE 2

Comparison with immunoenzymatic assay

The same determination (anti DNA antibodies) was effected as in example 1, but the incubation step with the specific ligand-ligand capable of reacting with erythrocytes coupling product was replaced by an incubation step with a specific ligand-enzyme coupling product incubation step; after incubation followed by washing, enzyme activity was determined.

Glucose oxidase ((Aspergillus niger)glucose oxidase (quality 1) supplied by Boehringer-Mannheim, GFR) was used as enzymes. The procedure for detecting this enzyme is described in detail in the following articles:
J. Histochem. Cytochem. 1979, 27, 1131–1139,
J. ALLERGY Clin. Immunol. 1978, 61, 23–27.

The results of these immunoenzymatic assays are given in table I.

These results show that the process of the invention provides results analogous to those obtained with the immunoenzymatic assaying process. The specificity of the assay was demonstrated by the absence of erythroadsorption when the serum containing very small amounts of anti-DNA antibodies were determined, or when a serum containing anti-DNA antibodies was previously incubated with an excess of DNA.

TABLE I

| | Assay of human anti DNA antibodies by immunoenzymatic assay and according to the process of the invention. | | | | | | |
|---|---|---|---|---|---|---|---|
| | Normal human serum | | | | Patient's serum | | | |
| serum dilution | immunoenzymatic assay* | assay according to the invention** | | | immunoenzymatic assay | assay according to the invention** | | |
| | | Av | Ab | Con A | | Av | Ab | Con A |
| 1/50 | 0.66 | − | + | + | 3.00 | +++ | ++++ | ++++ |
| 1/150 | 0.56 | − | ± | + | 2.65 | ++ | +++ | +++ |
| 1/450 | 0.33 | − | − | ± | 1.82 | − | ++ | ++ |
| 1/1350 | 0.10 | − | − | ± | 0.99 | − | ± | + |
| 1/4050 | 0.00 | − | − | − | 0.51 | − | − | ± |
| 1/12150 | 0.00 | − | − | − | 0.14 | − | − | ± |
| 1/36450 | 0.00 | − | − | − | 0.03 | − | − | − |
| control without serum | 0.00 | − | − | − | 0.00 | − | − | − |

*reagent used: human anti-immunoglobuline antibodies labelled with glucose oxidase.
**reagent used: coupling product of human anti Ig antibodies with avidin (Av), sheep red blood cell antibodies (Ab) and Concanavalin A(Con A).

We claim:

1. A process for the detection and assay of a biological substance by erythroadsorption, comprising:
   (1) immobilizing a compound which specifically binds the biological substance to be assayed;
   (2) incubating the immobilized compound with a liquid medium containing the biological substance to be assayed in order to fix said biological substance to the immobilized compound;
   (3) incubating the fixed biological substance with a soluble coupling product comprising: (a) a specific ligand, which binds to the fixed biological substance through (b) a coupling agent chosen from the group consisting of benzoquinone and glutaraldehyde, to (c) a second ligand which binds with erythrocytes;
   (4) eliminating excessive coupling product which is not bound to the fixed biological substance;
   (5) adding erythrocytes; and
   (6) determining the amount of erythrocytes bound to said coupling product.

2. Process according to claim 1, in which the biological substance to be assayed is an antigen, an antibody, a hapten, a hormone or an immunoglobulin.

3. A process according to either of claims 1 or 2, in which the specific ligand is an antigen or antibody and the second ligand is an antibody which binds to erythrocytes.

4. A process according to claim 1, in which determining the amount of erythrocytes is conducted by naked eye examination with comparison to standard samples.

5. A process according to claim 1, in which determining the amount of erythrocytes is determined by lysing adsorbed erythrocytes bound to the coupling product and quantitatively measuring the released hemoglobin.

6. A process according to claim 1, in which the liquid medium containing the biological substance to be assayed is a serum.

7. A process according to claim 6, in which said serum to be assayed is contacted, before said step of incubating with said immobilized compound, with red blood cells.

8. A process according to claim 7 in which the serum to be assayed is pretreated by the following steps:
  (a) treating red blood cells with a tanning agent;
  (b) adding said treated red blood cells to the serum to be assayed in an amount such that the concentration of the added treated red blood cells is about 10%;
  (c) stirring gently the mixture of the serum and treated red blood cells about one hour at a temperature of about 20° C. to about 25° C.; and
  (d) centrifuging, then collecting the serum to be assayed.

9. A process according to claim 1, in which the second ligand which binds with erythrocytes consists of antibodies which bind to erythrocytes.

10. The process of claim 1, wherein said erythrocytes are unmodified red blood cells.

11. The process of claim 1, wherein said process is performed in a heterogeneous phase.

12. A process according to claim 7, in which the serum to be assayed is pretreated by the following steps:
  (a) decomplementing the serum by heating at about 56° C. for about 30 minutes;
  (b) adding an excess of sheep red blood cells to said decomplemented serum obtaining a 10° red blood cell concentration;
  (c) leaving the decomplemented serum and red blood cells obtained in step (b) at a temperature from about 18° C. to about 25° C. for one hour with stirring; and
  (d) centrifuging the decomplemented serum to recover the serum and removing the residue of red blood cells.

* * * * *